(12) United States Patent
Kabuto et al.

(10) Patent No.: US 8,303,741 B2
(45) Date of Patent: Nov. 6, 2012

(54) PROCESS FOR PRODUCING PREPARATION FOR ORAL ADMINISTRATION

(75) Inventors: Akio Kabuto, Tokyo (JP); Yusaku Sugiura, Tokyo (JP); Eiji Suzuki, Tokyo (JP); Hideaki Okabe, Tokyo (JP)

(73) Assignee: Lintec Corporation, Tokyo (JP)

( * ) Notice: Subject to any disclaimer, the term of this patent is extended or adjusted under 35 U.S.C. 154(b) by 71 days.

(21) Appl. No.: 12/593,896

(22) PCT Filed: Dec. 14, 2007

(86) PCT No.: PCT/JP2007/074129
§ 371 (c)(1),
(2), (4) Date: Jan. 29, 2010

(87) PCT Pub. No.: WO2008/129730
PCT Pub. Date: Oct. 30, 2008

(65) Prior Publication Data
US 2010/0126650 A1 May 27, 2010

(30) Foreign Application Priority Data
Mar. 30, 2007 (JP) .................. 2007-092217

(51) Int. Cl.
B32B 38/00 (2006.01)
B32B 37/00 (2006.01)
B32B 38/08 (2006.01)

(52) U.S. Cl. ........ 156/60; 156/62.8; 156/221; 156/219; 156/242; 156/243; 424/493; 424/451; 424/494; 424/495; 424/496; 424/497

(58) Field of Classification Search .................. 156/60, 156/62.8, 221, 219, 242, 243; 424/493, 451, 424/494, 495, 496, 497
See application file for complete search history.

(56) References Cited

U.S. PATENT DOCUMENTS

| 4,882,169 A * | 11/1989 | Ventouras ............... 424/493 |
| 2002/0068088 A1 | 6/2002 | Gruber |
| 2004/0137040 A1 | 7/2004 | Nogami |
| 2006/0171990 A1* | 8/2006 | Asgari ..................... 424/426 |
| 2007/0141152 A1* | 6/2007 | Nogami .................... 424/472 |
| 2007/0298084 A1 | 12/2007 | Bracht et al. |

FOREIGN PATENT DOCUMENTS
EP  1 736 143 A1  12/2006
(Continued)

*Primary Examiner* — Katarzyna Wyrozebski Lee
*Assistant Examiner* — Daniel Lee
(74) *Attorney, Agent, or Firm* — Birch, Stewart, Kolasch & Birch, LLP

(57) ABSTRACT

A process for producing an oral preparation containing a first water-swellable gel-forming layer and a second water-swellable gel-forming layer as outermost layers, a medicine being sealed in an inner space formed by bonding the periphery of the first water-swellable gel-forming layer and the periphery of the second water-swellable gel-forming layer either directly or via an adhesive layer, the process including (a) a step of forming a first water-swellable gel-forming layer, (b) a step of forming a recess in a predetermined area of the first water-swellable gel-forming layer, (c) a step of filling the recess with a medicine to obtain a medicine-containing body, and (d) a step of forming a second water-swellable gel-forming layer over the medicine-containing body directly or via an adhesive layer so that the first water-swellable gel-forming layer and the second water-swellable gel-forming layer are bonded around the recess, and a process for continuously producing the oral preparation are disclosed. According to the above process for producing an oral preparation, an oral preparation in which the medicine is completely masked so that the medicine can be administered without a problem of bitterness and odor of the medicine can be efficiently produced without causing the medicine to deteriorate due to heat history, without a loss of the medicine, and without a limitation to the amount of the medicine to be added.

16 Claims, 5 Drawing Sheets

(A)

(B)

(C)

(D)

FOREIGN PATENT DOCUMENTS

| | | |
|---|---|---|
| JP | 57-114407 A | 7/1982 |
| JP | 61-161215 A | 7/1986 |
| JP | 2000-516222 A | 12/2000 |
| JP | 2005-289868 A | 10/2005 |
| JP | 2005-298471 A | 10/2005 |
| JP | 2007-044547 A | 2/2007 |
| WO | WO-02/087622 A1 | 11/2002 |
| WO | WO-2005/063217 A1 | 7/2005 |
| WO | WO-2005/074882 A2 | 8/2005 |

* cited by examiner (a)

(b)

(d3-i)

(d3-ii)

(a)

(b)

(a)

(b)

PROCESS FOR PRODUCING PREPARATION FOR ORAL ADMINISTRATION

TECHNICAL FIELD

The present invention relates to a process for efficiently producing an oral preparation which can be safely and easily administered without causing heat history and loss of the medicine.

BACKGROUND ART

An oral preparation may impart a displeasing feel (e.g., bitterness or astringency) due to the medicine or may cause nausea or medication refusal so that medication compliance may deteriorate. For example, a solid preparation (e.g., powder or tablet) which is a general form of an oral preparation can be swallowed only with difficulty if administered as is. Therefore, a solid preparation is usually administered together with a large amount of water, resulting in a decrease in medication compliance. In particular, elderly persons and children have difficulty in swallowing a solid preparation in many cases. In addition, the preparation may accidentally block the throat or become attached to the esophagus, which may cause an esophageal tumor.

In order to increase ease and safety of administration, an oral preparation a having water-swellable gel-forming layers 12 and 12' laminated on either side of a medicine 13 as shown in FIG. 10(a) has been proposed (Patent Documents 1 and 2).

When the oral preparation a is put into the patient's mouth, the water-swellable gel-forming layers are swollen and gelled by moisture such as saliva, whereby the preparation a changes into a form having a more easily administered size, shape, elasticity, viscosity, and the like and can be safely provided to elderly persons and infants without a danger of blocking the throat. In the case of a patient who can discharge only an insufficient amount of saliva to cause the water-swellable gel-forming layers to be sufficiently swollen and gelled, the preparation a can exhibit the same effect if administered together with a small amount of water or after being immersed in water. The amount of water used in such a case is very small as compared with the amount of water necessary for other solid preparations such as tablets and capsules.

When the oral preparation a is put into the patient's mouth, the water-swellable gel-forming layers are swollen and gelled by moisture such as saliva, causing the medicine-containing layer to be covered with the gel. The gel has an effect of masking the taste (bitterness, astringency, etc.) and odor of the medicine contained in the medicine-containing layer, whereby a decrease of medication compliance can be prevented.

However, the medicine 13 is exposed on the ends of the oral preparation a shown in FIG. 10(a). The medicine 13 in these areas cannot be completely covered with a gel and some portion is left exposed even if the water-swellable gel-forming layers 12 and 12' are swollen and gelled by moisture such as saliva. For this reason, it has been difficult to completely mask the taste and odor of the medicine 13 of the oral preparation a.

Therefore, another oral preparation which can completely mask the taste and odor of the medicine contained in the medicine-containing layer as shown in b of FIG. 10(b) has been proposed in Patent Document 3.

The oral preparation b described in Patent Document 3 is prepared as follows.

A suspension containing a water-swellable gel-forming agent and the like is applied to the surface of a first support such as a plastic film, and dried to form a water-swellable gel-forming layer 14'. A suspension containing an adhesive is applied to the surface of the water-swellable gel-forming layer 14', and dried to form an adhesive layer 15'. A first laminate in which the water-swellable gel-forming layer 14' and the adhesive layer 15' are sequentially laminated on the support can be obtained in this manner.

A second support is provided, and a water-swellable gel-forming layer 14 and an adhesive layer 15 are sequentially laminated on the surface of the second support. Next, a suspension containing a medicine and the like is applied to the surface of the adhesive layer 15, and dried to form a medicine 13. In this instance, the lower side of the medicine 13 is made smaller than the upper side of the adhesive layer 15. That is to say, the medicine 13 is formed at the center of the upper side of the adhesive layer 15 so that the periphery of the upper side of the adhesive layer 15 is left exposed. In this manner, a second laminate in which the water-swellable gel-forming layer 14, the adhesive layer 15, and the medicine 13 are sequentially laminated on the second support can be obtained.

Next, the periphery of the water-swellable gel-forming layer 14' of the first laminate is bonded to the periphery of the water-swellable gel-forming layer 14 via the adhesive layers 15 and 15' to obtain an oral preparation b having the medicine 13 sealed therein.

However, the above method of producing the oral preparation b allows only a limited amount of medicine to be included therein, and subjects the medicine to significant heat history by which the medicine may be denatured. In addition, the method of producing the oral preparation b has a problem of poor industrial productivity due to the requirement of making the lower side of the medicine 13 smaller than the upper side of the adhesive layer 15.

Patent Document 1: WO 02/087622
Patent Document 2: JP-A-2005-298471
Patent Document 3: JP-A-2005-289868

DISCLOSURE OF THE INVENTION

Problems to be Solved by the Invention

The present invention has been achieved in view of the above problems of the related art. An object of the present invention is to provide a process for efficiently producing an oral preparation in which the taste and odor of a medicine contained in a medicine-containing layer can be completely masked without heat history and product loss, as well as a process for continuously producing the same.

Means for Solving the Problems

The inventors of the present invention have conducted extensive studies in order to achieve the above object. As a result, the inventors have found that an oral preparation in which the taste and odor of a medicine contained in a medicine-containing layer are completely masked can be efficiently produced by forming a first water-swellable gel-forming layer on a support, forming recesses in predetermined areas of the first water-swellable gel-forming layer by embossing, filling the recesses with a medicine, and forming a second water-swellable gel-forming layer over the medicine so that the first water-swellable gel-forming layer and the second water-swellable gel-forming layer are bonded around the recesses. This finding has led to the completion of the present invention.

According to a first aspect of the present invention, the following process for producing an oral preparation is provided.

(1) A process for producing an oral preparation containing a first water-swellable gel-forming layer and a second water-swellable gel-forming layer as outermost layers, a medicine being sealed in an inner space formed by bonding the periphery of the first water-swellable gel-forming layer and the periphery of the second water-swellable gel-forming layer directly or via an adhesive layer, the process comprising:

(a) a step of forming a first water-swellable gel-forming layer;
(b) a step of forming a recess in a predetermined area of the first water-swellable gel-forming layer;
(c) a step of filling the recess with a medicine to obtain a medicine-containing body; and
(d) a step of forming a second water-swellable gel-forming layer over the medicine-containing body directly or via an adhesive layer so that the first water-swellable gel-forming layer and the second water-swellable gel-forming layer are bonded around the recess.

According to a second aspect of the present invention, the following process for continuously producing an oral preparation is provided.

(2) A process for continuously producing an oral preparation containing a first water-swellable gel-forming layer and a second water-swellable gel-forming layer as outermost layers, a medicine being sealed in an inner space formed by bonding the periphery of the first water-swellable gel-forming layer and the periphery of the second water-swellable gel-forming layer directly or via an adhesive layer, the process comprising:

(a3) a step of forming a first water-swellable gel-forming layer on a long first support;
(b3) a step of forming recesses in predetermined areas of the first water-swellable gel-forming layer;
(c3) a step of filling the recesses with a medicine to form a continuous band of a medicine-containing body; and
(d3) a step of forming a second water-swellable gel-forming layer over the medicine-containing body directly or via an adhesive layer so that the first water-swellable gel-forming layer and the second water-swellable gel-forming layer are bonded around the recesses.

Effect of the Invention

According to the process of the present invention, an oral preparation in which the medicine is completely masked so that the medicine can be administered without a problem of bitterness and odor can be efficiently produced without causing the medicine to deteriorate due to heat history, without a loss of the medicine, and without a limitation to the amount of the medicine to be added.

According to the continuous process of the present invention, an oral preparation in which the medicine is completely masked so that the medicine can be administered without a problem of bitterness and odor can be produced with high productivity without causing the medicine to deteriorate due to heat history, without a loss of the medicine, and without a limitation to the amount of the medicine to be added.

Figure 1:
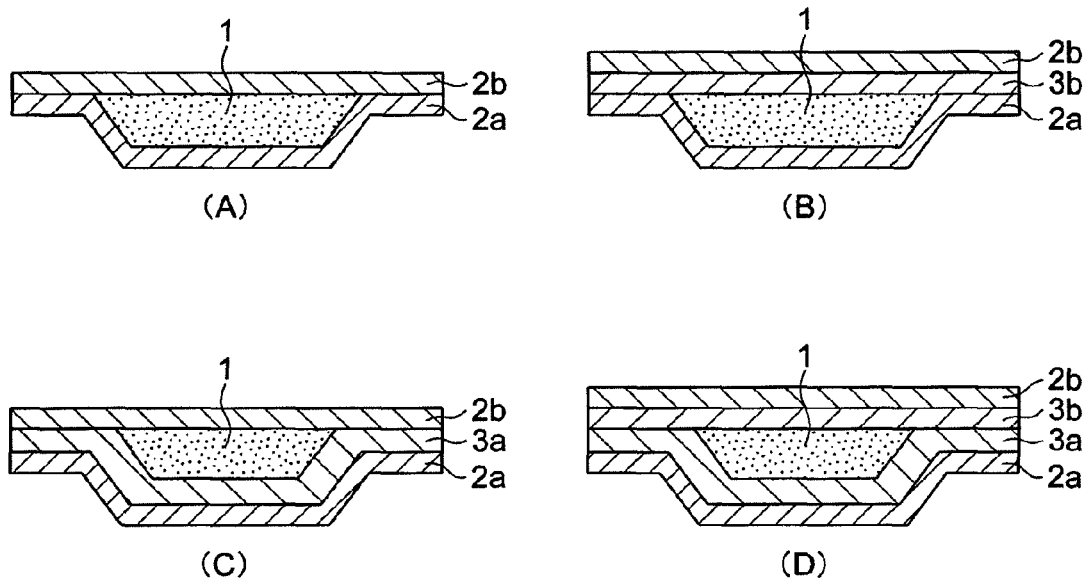
FIG. 1 is a cross-sectional view showing an oral preparation produced by the process of the present invention.

EXPLANATION OF SYMBOLS 1, 11, 13: Medicine
2a, 2b, 20a, 20b, 12, 12', 14, 14': Water-swellable gel-forming layer
3a, 3b, 30a, 30b, 15, 15': Adhesive layer
10, 100: Support
40: Recess
106, 400: Working roll
107, 500: Lower roll
100a: First support
100b: Second support
101a, 101b: Support delivery section
102a, 102b, 104a, 104b: Coating device
103b, 104a, 105b: Drier
108: Medicine feeder
109: Heat laminator
110a, 110b, 110e, 110f: Supporting roll
110c, 110d, 110g: Guide roll
110h, 110i: Press roll

BEST MODE FOR CARRYING OUT THE INVENTION

The present invention is described below in detail.

1) Process for Producing Oral Preparation

A process for producing an oral preparation according to the present invention produces an oral preparation containing a first water-swellable gel-forming layer and a second water-swellable gel-forming layer as outermost layers, a medicine being sealed in an inner space formed by bonding the periphery of the first water-swellable gel-forming layer and the periphery of the second water-swellable gel-forming layer directly or via an adhesive layer, the process comprising the following steps (a) to (d) in this order:

(a) a step of forming a first water-swellable gel-forming layer,
(b) a step of forming a recess in a predetermined area of the first water-swellable gel-forming layer,
(c) a step of filling the recess with a medicine to obtain a medicine-containing body, and
(d) a step of forming a second water-swellable gel-forming layer over the medicine-containing body directly or via an adhesive layer so that the first water-swellable gel-forming layer and the second water-swellable gel-forming layer are bonded around the recess.

FIG. 1 is a cross-sectional view showing an oral preparation produced by the process of the present invention.

In FIG. 1, an oral preparation (A) contains a medicine 1 and a first water-swellable gel-forming layer 2a directly laminated on one side of the medicine 1 and a second water-swellable gel-forming layer 2b directly laminated on the other side of the medicine 1. An oral preparation (B) contains a medicine 1 and a first water-swellable gel-forming layer 2a directly laminated on one side of the medicine 1 and a second water-swellable gel-forming layer 2b laminated on the other side of the medicine 1 via an adhesive layer 3b. An oral preparation (C) contains a medicine 1 and a first water-swellable gel-forming layer 2a laminated on one side of the medicine 1 via an adhesive layer 3a and a second water-swellable gel-forming layer 2b directly laminated on the other side of the medicine 1. An oral preparation (D) contains a medicine 1 and a first water-swellable gel-forming layer 2a laminated on one side of the medicine 1 via an adhesive layer 3a and a second water-swellable gel-forming layer 2b laminated on the other side of the medicine 1 via an adhesive layer 3b.

(I) Process for Producing Oral Preparations (A) and (B)

Figure 2:
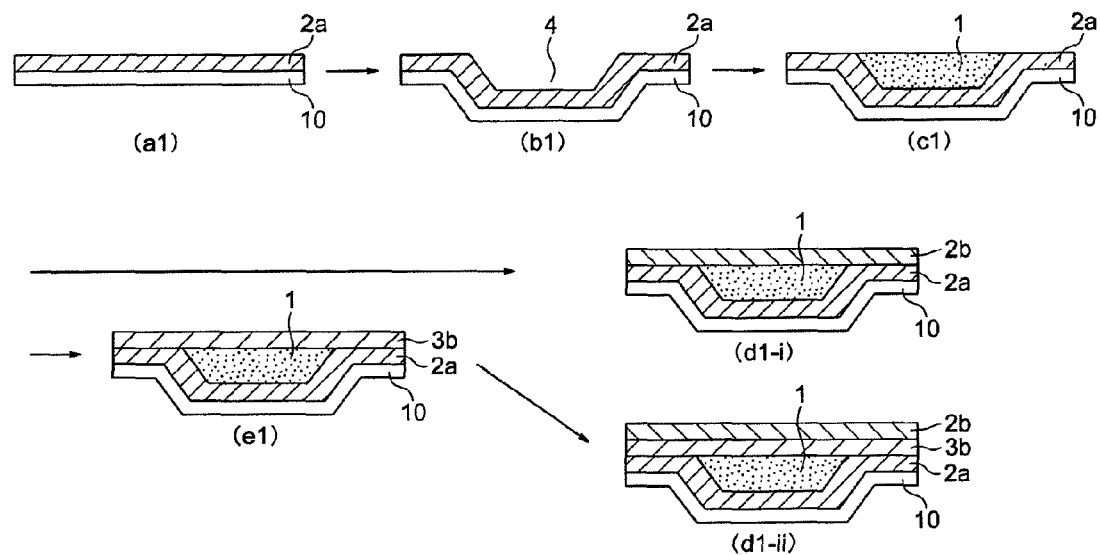
FIG. 2 is a cross-sectional view showing the steps of the process of the present invention.

FIG. 2 is a cross-sectional view showing the steps of the process for producing the oral preparations (A) and (B) shown in FIG. 1. The process for producing the oral preparations (A) and (B) will now be described with reference to FIG. 2.

[Step (a1)]

In the step (a1), the first water-swellable gel-forming layer 2a is formed on a support 10, as shown in FIG. 2(a1).

The support 10 is not particularly limited insofar as the water-swellable gel-forming layer can be formed on the surface of the support 10. As examples of the support 10, resin films such as a polyethylene terephthalate film, a polybuthylene terephthalate film, and a polypropylene film; papers such as a glassine paper, a clay coated paper, and a laminated paper (e.g., a polyethylene laminated paper), papers or resin films obtained by optionally treating these papers or resin films with a release agent such as a silicone type release agent, and the like can be given.

The water-swellable gel-forming layer contains a water-swellable gel-forming agent and can form a gel by swelling with moisture.

Any edible material which can form a gel by swelling with moisture can be used without particular limitations to the type. Either a crosslinked material or a non-crosslinked material may be used.

Specific examples of the water-swellable gel-forming agent include a carboxyvinyl polymer, starch and its derivatives, agar, alginic acid, arabino galactan, galactomannan, cellulose and its derivatives, carrageen, dextran, tragacanth, gelatin, pectin, hyaluronic acid, gellan gum, collagen, casein, xanthan gum, and the like.

Among these, a crosslinked carboxyvinyl polymer is preferable due to the capability of exhibiting appropriate gel strength during swelling, with crosslinked polyacrylic acid being particularly preferable.

A crosslinking agent appropriate for the molecules to be crosslinked may be used for crosslinking. For example, the carboxyvinyl polymers may be crosslinked using a polyvalent metal compound. As specific examples of the polyvalent metal compounds, calcium chloride, magnesium chloride, aluminum chloride, aluminum sulfate, potassium alum, iron chloride alum, ammonium alum, ferric sulfate, aluminum hydroxide, aluminum silicate, aluminum phosphate, iron citrate, magnesium oxide, calcium oxide, zinc oxide, and zinc sulfate can be given.

The content of the water-swellable gel-forming agent in the water-swellable gel-forming layer is appropriately adjusted according to the type of the water-swellable gel-forming agent usually in the range of 15 to 70 wt % of the water-swellable gel-forming layer.

A film-forming agent may be added to the water-swellable gel-forming layer to promote the film forming capability.

Any material having film-forming capability can be used as the film-forming agent without a particular limitation. Examples of the film-forming agent that can be used include polyvinyl alcohol; polyvinylpyrrolidone; polyvinyl acetate; polyvinyl acetate phthalate; hydroxyalkyl celluloses such as hydroxypropyl cellulose, hydroxypropylmethyl cellulose, hydroxymethyl cellulose, and hydroxyethyl cellulose; alkyl celluloses such as methyl cellulose and ethyl cellulose; carboxyalkyl celluloses such as carboxymethyl cellulose; acrylic esters; methacrylic esters; and the like.

Among these, water-soluble film-forming agents are preferable. If the film-forming agent is water-soluble, moisture can easily enter the water-swellable gel-forming layer and accelerate swelling of the water-swellable gel-forming layer and gel formation in the mouth.

As examples of the water-soluble film-forming agent, polyvinyl alcohol; hydroxyalkyl celluloses such as hydroxypropyl cellulose and hydroxypropylmethyl cellulose; methylcellulose; polyvinylpyrrolidone; and the like can be given. Among these, polyvinyl alcohol is particularly preferable due to its capability of functioning as a masking agent which will be later described.

The content of the film-forming agent is not particularly limited, but is usually 30 to 85 wt % of the water-swellable gel-forming layer to be formed.

A plasticizer may be added to the water-swellable gel-forming layer in order to provide the water-swellable gel-forming layer with moderate flexibility.

As examples of the plasticizer that can be used, propylene glycol, polyethylene glycol, glycerol and sorbitol, glycerin triacetate, diethyl phthalate and triethyl citrate, lauryl acid, sucrose, sorbitol, and the like can be given.

A masking agent may be added to the water-swellable gel-forming layer in order to mask the taste and odor of the medicine. The addition of the masking agent improves the effect of masking the taste and odor imparted by the water-swellable gel-forming layer, whereby a decrease in medication compliance can be efficiently prevented.

As examples of the masking agent that can be used, masking agents for providing acidity such as citric acid, tartaric acid, and fumaric acid; sweeteners such as saccharin, glycyrrhizic acid, white sugar, fructose, and mannitol; fresheners such as menthol and peppermint oil; natural or synthetic perfumes; and the like can be given.

Other additives such as antiseptic agents (e.g., methyl hydroxybenzoate and propyl hydroxybenzoate); coloring agents such as an edible lake coloring agent; and the like may be added if desired. The addition of these additives can reduce the hardness of the water-swellable gel-forming layer which has been formed as a film, whereby water can easily enter the water-swellable gel-forming layer. The water accelerates swelling of the water-swellable gel-forming layer and gel formation.

The water-swellable gel-forming layer 2a can be formed by forming a coating of a composition for forming the water-swellable gel-forming layer on the support 10 by applying the composition using a known coating device such as a gravure coater, a knife coater, a roll coater, a die coater, and an applicator or spraying the composition using a known spraying device, and drying the coating to remove the solvent.

The composition for forming the water-swellable gel-forming layer can be prepared by mixing a water-swellable gel-forming agent, a solvent, and additives such as a film-forming agent which are optionally used, and stirring the mixture.

The solvent used for preparing the composition for forming the water-swellable gel-forming layer may be appropriately selected according to the type of the solutes. As specific examples of such a solvent, purified water, ethanol, and a mixed solvent of these can be given.

Although the amount of the solvent used differs according to the type of the water-swellable gel-forming agent, the solvent is usually used in an amount of 1 to 100 parts by weight, and preferably 5 to 50 parts by weight for 1 part by weight of the water-swellable gel-forming agent.

The temperature employed when drying the coating of the composition for forming the water-swellable gel-forming layer is usually 50 to 120° C., and preferably 60 to 90° C. The drying time is usually 1 to 15 minutes, and preferably 1 to 10 minutes.

The basis weight of the water-swellable gel-forming layer 2a that is formed is usually 3 to 1000 g/m$^2$, and preferably 5 to 500 g/m$^2$. If the basis weight of the water-swellable gel-forming layer is less than 3 g/m$^2$, gel formation is not enough and the effect of masking the taste and odor of the medicine by the water-swellable gel-forming layer is insufficient. If the basis weight of the water-swellable gel-forming layer is more than 1000 g/m$^2$, the oral preparation cannot be administered with ease because the water-swellable gel-forming layer does not swell sufficiently with only saliva and cannot form a gel by merely putting the preparation into the mouth.

[Step (b1)]

In the step (b1), a recess is formed in a predetermined area of the water-swellable gel-forming layer 2a, as shown in FIG. 2(b1). The recess can be efficiently filled with the medicine without loss, as described later.

As a method for forming the recess in a predetermined area of the water-swellable gel-forming layer 2a, a method of pressing the predetermined area of the water-swellable gel-forming layer 2a can be given.

There are no particular limitations to the shape of the recess. The shape of the recess may be round, square, or polygonal when observed from above.

The volume of the recess may be appropriately determined according to the amount, use, and the like of the medicine described later. The recess usually has a diameter of 5 to 50 mm and a depth of 0.2 to 10 mm, and preferably has a diameter of 5 to 20 mm and a depth of 0.3 to 6 mm.

Although there are no particular limitations to the method of pressing a predetermined area of the water-swellable gel-forming layer 2a in order to form the recess, an embossing method is preferable from the viewpoint of working efficiency.

Embossing is a method of producing recesses and projections on the surface of a sheet by die pressing or the like.

Prior to embossing, it is preferable to laminate a protective film on the water-swellable gel-forming layer 2a in order to protect the surface of the water-swellable gel-forming layer 2a.

As examples of the protective film, resin films such as a polyethylene terephthalate film, a polybuthylene terephthalate film, and a polypropylene film; papers such as a glassine paper, a clay coated paper, and a laminated paper (e.g., a polyethylene laminated paper), papers or resin films obtained by optionally treating these papers or resin films with a release agent such as a silicone type release agent, and the like can be given.

The protective film can be removed before filling the recess with the medicine in the next step.

[Step (c1)]

In the step (c1), the recess formed in the previous step is filled with a medicine 1 to obtain a medicine-containing body, as shown in FIG. 2(c1).

The medicine 1 is administered to patients. There are no particular limitations to the type of the medicine 1. Examples of medicines which act on the central nerves include hypnotics such as amobarbital, estazolam, triazolam, nitrazepam, and pentobarbital; psychotropic drugs such as amitriptyline hydrochloride, imipramine hydrochloride, oxazolam, chlordiazepoxide, chlorpromazine, diazepam, sulpiride, and haloperidol; antiparkinson drugs such as trihexyphenidyl and levodopa; analgesic and antiinflammatory agents such as aspirin, isopropylantipyrine, indomethacin, diclofenac sodium, mefenamic acid, streptokinase, streptodornase, serrapeptase, and pronase; and central nerve system metabolism activators such as ATP and vinpocetine.

Examples of medicines which act on respiratory organs include expectorants such as carbocysteine and bromhexin hydrochloride; anti-asthma drugs such as azelastine hydrochloride, oxatomide, theophylline, terbutaline sulfate, tranilast, procaterol hydrochloride, and ketotifen fumarate.

Examples of medicines which act on the circulatory organs include cardiotonic drugs such as aminophylline, digitoxin, and digoxin; antiarrhythmic drugs such as ajmaline, disopyramide, procainamide hydrochloride, and mexiletine hydrochloride; antianginal drugs such as amyl nitrite, alprenolol hydrochloride, isosorbide nitrate, nicorandil, oxyfedrine, dipyridamole, dilazep hydrochloride, diltiazem hydrochloride, glycerol trinitrate, nifedipine, and verapamil hydrochloride; peripheral vasodilating drugs such as kalliginogenase; antihypertensive drugs such as atenolol, captopril, clonidine hydrochloride, metoprolol tartrate, spironolactone, triamterene, trichloromethiazide, nicardipine, hydralazine hydrochloride, hydrochlorothiazide, prazosin hydrochloride, furosemide, propranolol hydrochloride, enalapril malate, methyldopa, labetalol hydrochloride, and reserpine; and antiarteriosclerotic drugs such as clofibrate, dextran sulfate, nicomol, and niceritrol.

Examples of blood and hematogenous agents include hemostatic drugs such as sodium carbazochrom sulfonate and tranexamic acid; and antithrombosis drugs such as ticlopidine hydrochloride and warfarin potassium.

Examples of medicines which act on the digestive system include antiulcer drugs such as azulene, aldioxa, cimetidine, ranitidine hydrochloride, famotidine, teprenone, and rebamipide; antiemetics such as domperidone and metoclopramide; cathartics such as sennoside; digestive enzyme preparations; and anti-hepatic drugs such as glycyrrhizin and liver extract preparations.

Examples of medicines which act on a metabolic disease include antidiabetics such as glibenclamide, chlorpropamide, and tolbutamide; antipodagrics such as allopurinol and colchicines.

Examples of medicines in the ophthalmologic field include acetazolamide.

Examples of medicines in the otolaryngology field include antidizziness drugs such as difenidol hydrochloride and betahistine mesylate.

Examples of chemotherapeutic agents and antibiotics include isoniazid, ethambutol hydrochloride, ofloxacin, erythromycin stearate, cefaclor, norfloxacin, fosfomycin calcium, minocycline hydrochloride, rifampicin, rokitamycin, and the like.

Examples of antineoplastic agents include cyclophosphamide, tegafur, and the like.

Examples of immunosuppressants include azathioprine and the like. Examples of hormones and an internal secretion curative medicines include progestational hormone, salivary gland hormone, thiamazole, prednisolone, betamethasone, liothyronine, and levothyroxine.

Examples of in vivo activation substances (autacoid) include antihistaminics such as clemastine fumarate and chlorpheniramine D-maleate; and vitamins such as alfacalcidol, cobamamide, tocopherol nicotinate, and mecobalamin.

These medicines may be used either individually or in combination of two or more.

There are no specific limitations to the form of the medicine. Any forms such as a tablet, a powder, and the like can be used.

The recess formed in the above step (c1) is filled with the medicine. When embossing is applied in the step (c1), the embossed area is filled with the medicine.

The medicine may contain various pharmacologically acceptable additives such as a substrate (e.g., thermoplastic edible polymers), an excipient, a binder, a disintegrator, a masking reagent, a coloring agent, and the like.

The amount of the medicine with which the recess is filled is 0.01 mg to 10 g per one dosage of the oral preparation, for example.

[Step (d1)]

In the step (d1), a water-swellable gel-forming layer 2b is formed over the medicine-containing body directly or via an adhesive layer so that the water-swellable gel-forming layers are bonded around the recess.

The state of the oral preparation obtained in this step is shown in FIG. 2(d1-i) and FIG. 2(d1-ii). FIG. 2(d1-i) shows a structure obtained by forming the water-swellable gel-forming layer 2b on the medicine-containing body obtained in the step (c1) directly so that the water-swellable gel-forming layers are bonded around the recess (step (d1-i)).

FIG. 2(d1-ii) shows a structure obtained by forming a water-swellable gel-forming layer 2b on the medicine-containing body obtained in the step (c1) via an adhesive layer 3b so that the water-swellable gel-forming layers are bonded around the recess (step (d1-ii)).

Of these, the step (d1-ii) is preferable as the step (d1) to ensure stronger adhesion.

In the step (d1-i), the water-swellable gel-forming layer 2b may be formed by the following method ($\alpha$) or ($\beta$) so that the water-swellable gel-forming layers are bonded around the recess.

($\alpha$): In the same manner as the method of forming the water-swellable gel-forming layer 2a on the support 10 in the step (a1), this method includes applying a composition for forming the water-swellable gel-forming layer to the side of the medicine-containing body on which the medicine is exposed by coating using an applicator or the like, or by spraying, and drying the coating.

($\beta$): This method includes providing a separate support, forming a water-swellable gel-forming layer 2b on the support in the same manner as in the step (a1) to obtain a laminate, thermally bonding the water-swellable gel-forming layer 2b of the laminate to the side of the medicine-containing body on which the medicine is exposed, and removing the support.

Of these, the method ($\beta$) is preferable due to less heat history and, therefore, a smaller risk of medicine deterioration.

The bonding temperature employed in the method ($\beta$) is usually 50 to 250° C., and preferably 80 to 180° C. The pressure applied during bonding is usually $9.8 \times 10^4$ Pa.

As examples of the composition for forming the water-swellable gel-forming layer 2b, the same compositions as used in forming the water-swellable gel-forming layer 2a can be given.

In the step (d1-ii), any pharmaceutically acceptable adhesive may be used for forming the adhesive layer 3b. For example, an adhesive which exhibits adhesiveness when used together with a solvent, a heat-sealable adhesive which exhibits adhesiveness upon heating, or the like may be used. These adhesives may be used either individually or in combination of two or more.

As examples of the adhesive exhibiting adhesiveness when used together with a solvent, polyacrylic acids such as carboxyvinyl polymer and sodium polyacrylate, or their pharmacologically acceptable nontoxic salts; an acrylate copolymer or its pharmacologically acceptable nontoxic salts; hydrophilic cellulose derivatives such as carboxymethylcellulose and sodium salt thereof; pullulan, povidone, karaya gum, pectin, xanthan gum, traganth, alginic acid, gum arabic, acid polysaccharides, their derivative and their pharmacologically acceptable salts; and the like can be given.

As examples of the heat-sealable adhesive, homopolymers such as polyvinyl acetate and polyvinylpyrrolidone; copolymers such as a copolymer of vinyl acetate and vinyl pyrrolidone; and the like can be given.

When using the adhesive which exhibits adhesiveness when used together with a solvent, the solvent in the coating produced by applying a composition for forming an adhesive layer is not removed immediately after the application, but removed afterward when the periphery of the recess is bonded in the later-described step (d1-ii).

The adhesive layer 3b can be formed as shown in FIG. 2(e1) by forming a coating of a composition for forming an adhesive layer on the medicine-containing body by applying the composition using a known coating device or spraying the composition using a known spraying device, and drying the coating to remove the solvent.

The composition for forming an adhesive layer can be prepared by mixing an adhesive, a solvent, and additives which are optionally used, and stirring the mixture.

As the additives which may be added, a plasticizer and the like can be given. As the plasticizer, the same plasticizers that have been mentioned as the plasticizer to be used in the water-swellable gel-forming layer can be used.

The solvent is appropriately selected according to the type of the solute. As specific examples, purified water, ethanol, and the like can be given.

Although the amount of the solvent used differs according to the type of the adhesive, the solvent is usually used in an amount of 1 to 10 parts by weight, and preferably 2 to 5 parts by weight for 1 part by weight of the adhesive.

The temperature employed when drying the coating of the composition for forming an adhesive layer is usually 50 to 120° C., and preferably 60 to 90° C. The drying time is usually 1 to 15 minutes, and preferably 1 to 10 minutes.

The basis weight of the adhesive layer 3b is appropriately adjusted in an orally doable range, which is usually 1 to 50 $g/m^2$, and preferably 10 to 30 $g/m^2$. If the basis weight of the adhesive layer 3b is less than 1 $g/m^2$, bonding may be insufficient. On the other hand, if the basis weight of the adhesive layer 3b is more than 50 $g/m^2$, swelling of the oral preparation by saliva and the like may be inhibited. In addition, when the adhesive contained in the adhesive layer 3b is insoluble in water, the preparation may impart an unfavorable sensation when administered.

The water-swellable gel-forming layer 2b is formed on the adhesive layer 3b formed in this manner so that the water-swellable gel-forming layers are bonded around the recess.

As examples of the composition for forming the water-swellable gel-forming layer 2b, the same compositions as used in forming the water-swellable gel-forming layer 2a can be given.

In the step (d1-ii), the water-swellable gel-forming layer 2b may be formed on the adhesive layer 3b by the following method (γ) or (δ) so that the water-swellable gel-forming layers are bonded around the recess, for example.

(γ): This method includes forming a coating of the composition for forming an adhesive layer on the side of the medicine-containing body on which the medicine is exposed, drying the coating to form the adhesive layer 3b, forming a coating of the composition for forming the water-swellable gel-forming layer on the adhesive layer 3b, and drying the coating to obtain the water-swellable gel-forming layer 2b.

(δ): This method includes providing a separate support, forming a laminate of the water-swellable gel-forming layer 2b and the adhesive layer 3b on the support, thermally bonding the adhesive layer 3b of the laminate to the side of the medicine-containing body on which the medicine is exposed, and removing the support.

Of these methods, the method (δ) is preferable due to less heat history and, therefore, a smaller risk of medicine deterioration.

The bonding temperature employed for the method (δ) is usually 50 to 250° C., and preferably 80 to 180° C. The pressure applied during bonding is usually $9.8 \times 10^4$ Pa.

The basis weight of the water-swellable gel-forming layer 2b that is formed is usually 3 to 1000 g/m$^2$, and preferably 5 to 500 g/m$^2$.

(II) Process for Producing Oral Preparations (C) and (D)

Figure 3:
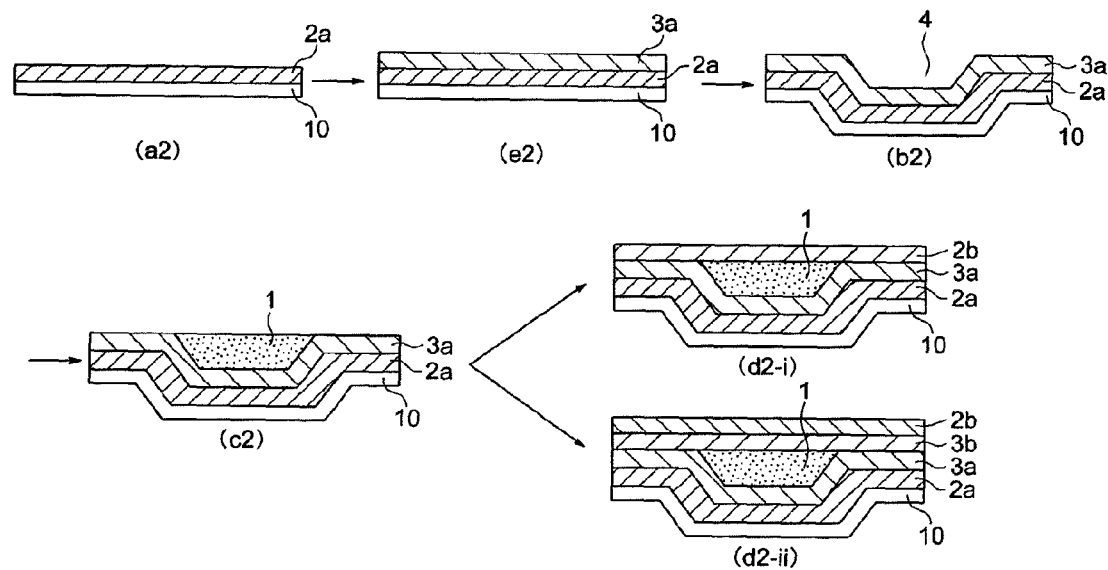
FIG. 3 is a cross-sectional view showing the steps of the process of the present invention.

FIG. 3 shows the process for producing the oral preparations (C) and (D) shown in FIG. 1. The process for producing the oral preparations (C) and (D) will now be described with reference to FIG. 3.

[Step (a2)]

In the step (a2), a water-swellable gel-forming layer 2a is formed on a support 10, as shown in FIG. 3(a2). The details of the step (a2) are the same as the step (a1) of the process for producing the oral preparations (A) and (B).

[Step (e2)]

In the step (e2), an adhesive layer 3a is formed on the water-swellable gel-forming layer 2a, as shown in FIG. 3(e2).

The adhesive layer 3a may be formed by forming a coating of a composition for forming an adhesive layer on the water-swellable gel-forming layer 2a by applying the composition for forming an adhesive layer which contains at least an adhesive using a known coating device such as an applicator or spraying the composition using a known spraying device, and drying the coating, for example.

As the composition for forming an adhesive layer that can be used, the same compositions used for forming the adhesive layer 3b mentioned above can be given.

The temperature used for drying the coating of the composition for forming an adhesive layer is usually 50 to 120° C., and preferably 60 to 90° C. The drying time is usually 1 to 15 minutes, and preferably 1 to 10 minutes.

[Step (b2)]

In the step (b2), a recess is formed in a predetermined area of the adhesive layer 3a which has been formed on the water-swellable gel-forming layer 2a as shown in FIG. 3(b2). The recess can be efficiently filled with the medicine without loss, as described later.

As the method for forming the recess in a predetermined area of the adhesive layer 3a, a method of pressing the predetermined area of the adhesive layer 3a from the surface-side can be given.

There are no particular limitations to the shape of the recess. The shape of the recess may be round, square, or polygonal when observed from above.

The volume of the recess may be appropriately determined according to the amount, use, and the like of the medicine described later. The recess usually has a diameter of 5 to 50 mm and a depth of 0.2 to 10 mm, and preferably has a diameter of 5 to 20 mm and a depth of 0.3 to 6 mm.

Although there are no particular limitations to the method of pressing the predetermined area of the adhesive layer 3a in order to form the recess, a method of embossing is preferable from the viewpoint of working efficiency.

Embossing is a method of producing recesses and projections on the surface of a sheet by die pressing and the like.

Prior to embossing, it is preferable to laminate a protective film on the adhesive layer 3a in order to protect the surface of the adhesive layer 3a.

As the protective film, the same protective film mentioned above can be given.

[Step (c2)]

In the step (c2), the recess formed in the previous step is filled with a medicine 1 to obtain a medicine-containing body, as shown in FIG. 3(c2).

The medicine 1 is administered to patients. There are no particular limitations to the type of the medicine 1. As the medicine, the same compounds as mentioned above can be given.

The recess formed in the step (b2) is filled with the medicine. When embossing is applied in the step (b2), the embossed area is filled with the medicine.

[Step (d2)]

In the step (d2), a water-swellable gel-forming layer 2b is formed on the medicine-containing body directly or via an adhesive layer so that the water-swellable gel-forming layers are bonded around the recess.

The state of the oral preparation obtained in this step is shown in FIG. 3(d2-i) and FIG. 3(d2-ii). FIG. 3(d2-i) shows a structure obtained by forming the water-swellable gel-forming layer 2b on the medicine-containing body obtained in the step (c2) directly so that the water-swellable gel-forming layers are bonded around the recess (step (d2-i)).

FIG. 2(d2-ii) shows a structure obtained by forming the water-swellable gel-forming layer 2b on the medicine-containing body obtained in the step (c2) via an adhesive layer 3b so that the water-swellable gel-forming layers are bonded around the recess (step (d2-ii)).

Of these, the step (d2-ii) is preferable as the step (d2) to ensure stronger adhesion.

The steps (d2-i) and (d2-ii) can be performed in the same manner as the above-mentioned steps (d1-i) and (d1-ii) shown in FIG. 2.

2) Process for Continuously Producing Oral Preparation

A process for continuously producing an oral preparation according to the present invention continuously produces an oral preparation containing a first water-swellable gel-forming layer and a second water-swellable gel-forming layer as outermost layers, a medicine being sealed in an inner space formed by bonding the periphery of the first water-swellable gel-forming layer and the periphery of the second water-swellable gel-forming layer directly or via an adhesive layer, the process comprising (a3) a step of forming a first water-swellable gel-forming layer on a long first support, (b3) a step of forming recesses in predetermined areas of the first water-swellable gel-forming layer, (c3) a step of filling the recesses with a medicine to form a continuous band of a medicine-containing body, and (d3) a step of forming a second water-swellable gel-forming layer over the medicine-containing body directly or via an adhesive layer so that the first water-swellable gel-forming layer and the second water-swellable gel-forming layer are bonded around the recesses.

A step (e3) of forming an adhesive layer on the first water-swellable gel-forming layer may be provided between the step (a3) and the step (b3).

According to the continuous process of the present invention, an oral preparation having the same structure as the preparation obtained by the above process of the present invention can be produced continuously and efficiently.

Figure 4:
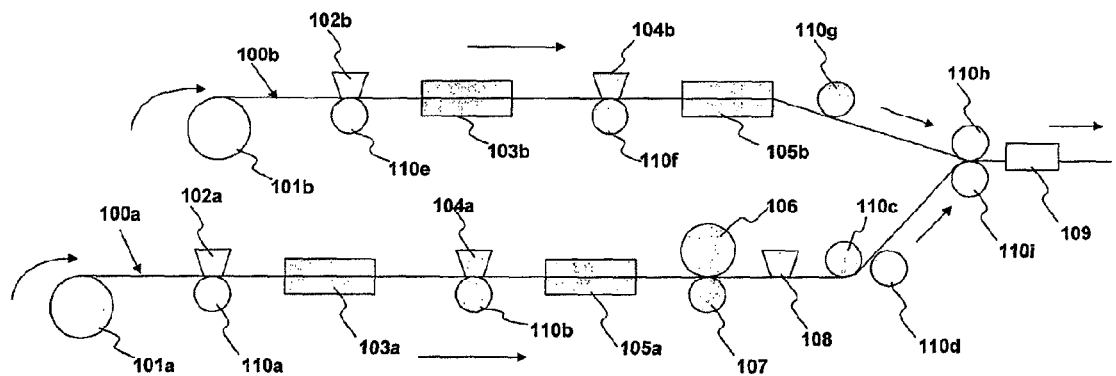
FIG. 4 is a schematic diagram showing a continuous production device used for the continuous process of the present invention.

The continuous process of the present invention may be carried out using an oral preparation continuous production device shown in FIG. 4, for example.

The continuous process of the present invention is described below with reference to FIG. 4.

In FIG. 4, symbols 110a, 110b, 110e, and 110f indicate supporting rolls, symbols 110c, 110d, and 110g indicate guide rolls, symbols 110h and 110i indicate press rolls.

[Step (a3)]

A rolled-up long first support 100a is continuously fed from a support delivery section 101a and forwarded in a given direction, while applying a composition for forming a water-swellable gel-forming layer to the support 100a using a coating device 102a to form a coating of the composition on the support 100a. The coating is dried in a drier 103a to form a water-swellable gel-forming layer 20a. A structure having the cross-section shown in FIG. 5(a3) is thus obtained.

As the long first support 100a, the same material as the support 10 having a long size may be used.

The size (length, breadth, etc.) of the first support 100a may be appropriately determined according to the type of the oral preparation, production scale, production efficiency, and the like. The first support 100a may have a breadth that allows production of the oral preparations in one line or several lines.

As a composition which can be used for forming the water-swellable gel-forming layer, the same compositions mentioned above in the process for producing the oral preparation can be given.

[Step (e3)]

Figure 5:
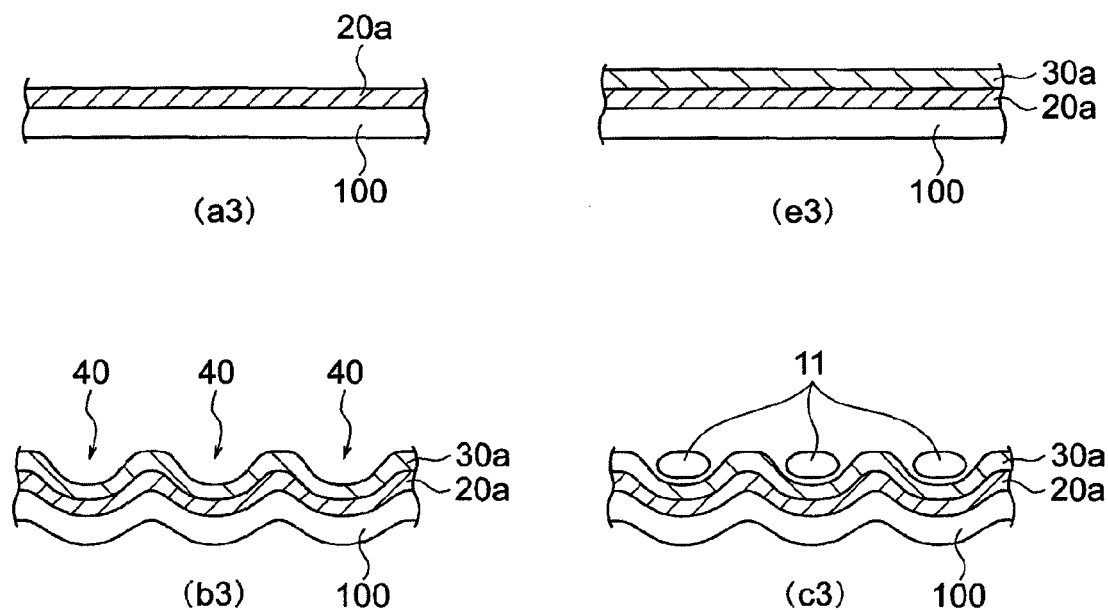
FIG. 5 is a cross-sectional view showing the steps of the continuous process of the present invention.

An adhesive layer 30a is formed on the water-swellable gel-forming layer 20a formed in the step (a3) to obtain a structure having a cross-section shown in FIG. 5(e3).

Specifically, a coating of the composition for forming an adhesive layer is formed by applying the composition using a coating device 104a while delivering the structure on which the water-swellable gel-forming layer 20a is formed in a given direction. The coating is dried in a drier 105a to form an adhesive layer 30a on the water-swellable gel-forming layer 20a. A structure shown in FIG. 5(e3) is thus obtained.

As the composition which can be used for forming the adhesive layer, the same compositions mentioned above in the process for producing the oral preparation can be given.

[Step (b3)]

A plurality of recesses 40 with a specific shape are formed in predetermined areas of the adhesive layer 30a to obtain a structure shown in FIG. 5(b3).

Figure 6:
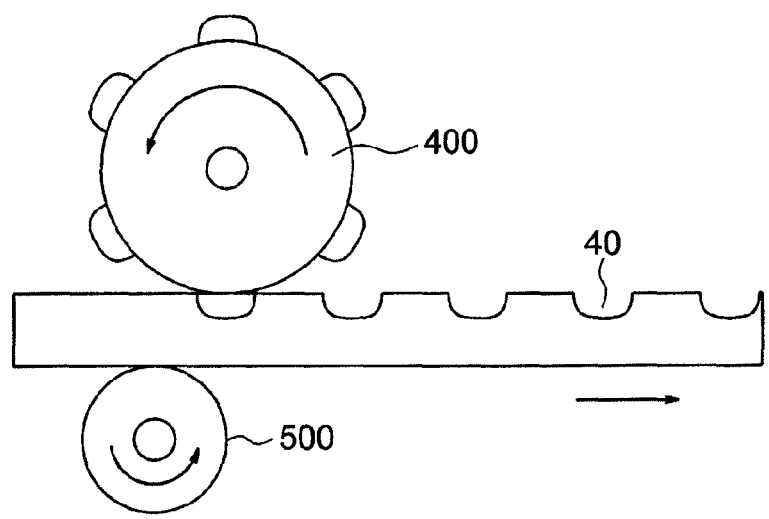
FIG. 6 is a view showing an embossing method.

Specifically, the structure shown in FIG. 5(b3) can be obtained by embossing the surface of the adhesive layer 30a using a press roll 400 and a lower roll 500 (106 and 107 in FIG. 4) having two or more projections as shown in FIG. 6, for example, while delivering in a certain direction the structure with the adhesive layer 30a formed thereon to continuously form two or more recesses 40 in the predetermined areas of the adhesive layer 30a.

Although the lower roll 500 shown in FIG. 6 has a flat surface, a lower roll provided with recesses with a surface configuration corresponding to the projections of the press roll 400 may be used.

The shape, depth, volume, and the like of the recess may be determined according to the type, the amount, and the like of the medicine filled therein. The number of recesses formed in the transverse direction may be appropriately determined according to the type of the medicine, usage of the oral preparation, production scale, production efficiency, and the like.

Recesses having a specific shape can be formed continuously, easily, and efficiently by utilizing the above method.

Figure 7:
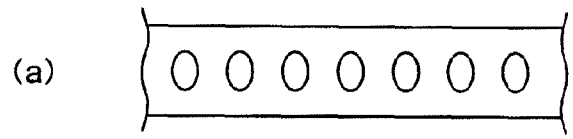
FIG. 7 are plan views showing an example of an embossed long film.
Figure 7:
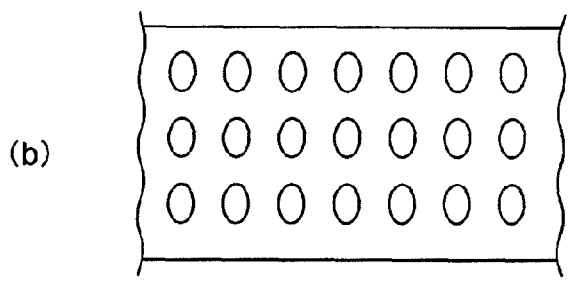

FIG. 7 is a plan view showing an example of a long sheet in which recesses 40 are formed. The sheet shown in FIG. 7(a) has round recesses formed in one transverse row. The sheet shown in FIG. 7(b) has round recesses formed in three transverse rows.

It is preferable to emboss the sheet after laminating a protective film on the adhesive layer 30a to protect the surface of the adhesive layer 30a. As the protective film, the same protective films mentioned above in the process for producing the oral preparation of the present invention can be given.

[Step (c3)]

The recesses 40 are continuously filled with a medicine 11 from the medicine feeder 108 to obtain a medicine-containing body in the form of a band having a cross-sectional structure shown in FIG. 5(c3).

As the medicine with which the recesses are filled, the same medicines mentioned above in the process for producing the oral preparation of the present invention can be given. There are no specific limitations to the form of the medicine. A medicine in the form of either a powder or a tablet may be used.

[Step (d3)]

Figure 8:
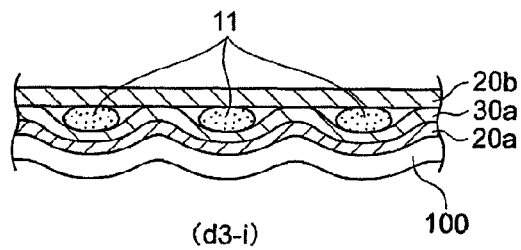
FIG. 8 is a cross-sectional view showing an oral preparation produced by the continuous process of the present invention.
Figure 8:
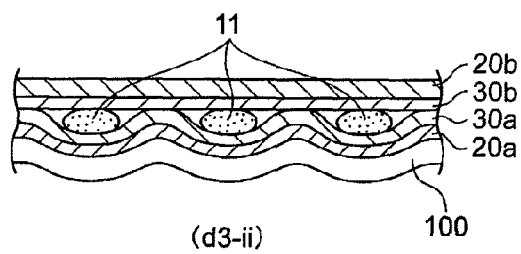

An oral preparation having a cross-sectional structure shown in FIG. 8(d3-i) or FIG. 8(d3-ii) can be obtained by forming a water-swellable gel-forming layer 20b on the medicine-containing body directly or via an adhesive layer 30b so that the water-swellable gel-forming layers are bonded around the recesses.

Specifically, the step (d3) may be carried out in the same manner as in the method for obtaining a laminate having a cross-sectional structure shown in FIG. 3(d2-i) or FIG. 3(d2-ii).

For example, as shown in FIG. 4, a rolled-up long second support 100b is continuously fed from the support delivery section 101b and forwarded in a given direction, while applying a composition for forming a water-swellable gel-forming layer to the support 100b using a coating device 102b to form a coating of the composition on the support 100b. The coating is dried in a drier 103b to form a water-swellable gel-forming layer 20b.

A composition for forming an adhesive layer is applied using a coating device 104b to form a coating of the composition. The coating is then dried using a drier 105b to form an adhesive layer 30b on the water-swellable gel-forming layer 20a. A structure having the same cross-sectional structure as that shown in FIG. 5(e3) is thus obtained.

Then, the medicine-containing body in the form of a band obtained as described above and the structure having the cross-section shown in FIG. 5(e3) are sent between the press rolls 110h and 110i so that the adhesive layer 30a and the adhesive layer 30b are attached, and are thermally bonded using a heat laminator 109, thereby obtaining a long sheet of oral preparations having a cross-sectional structure shown in FIG. 8(d3-ii).

The bonding temperature is usually 50 to 250° C., and preferably 80 to 180° C. The pressure applied during bonding is usually $9.8 \times 10^4$ Pa.

Although the device shown in FIG. 4 is used for continuous production of the oral preparations having a cross-sectional structure shown in FIG. 8(d3-ii), it is possible to produce a long sheet of oral preparations having a cross-sectional structure shown in FIG. 8(d3-i) if the coating device 104b for applying the composition for forming an adhesive layer and the drier 105b shown in FIG. 4 are omitted.

In this case, the bonding temperature and the bonding pressure are the same as described above.

The long sheet of the oral preparations obtained in this manner is usually die-cut to a predetermined size and separated from the support.

Figure 9:
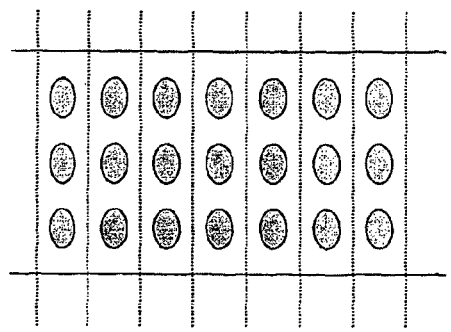
FIG. 9 is a view showing a method of die-cutting a long film of the oral preparation.
Figure 9:
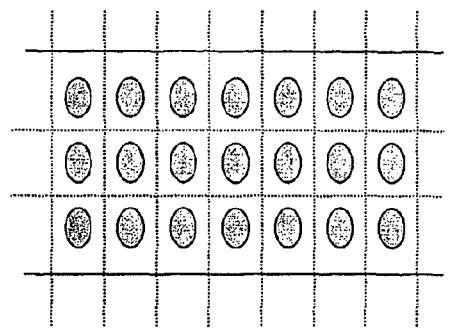
Figure 10:
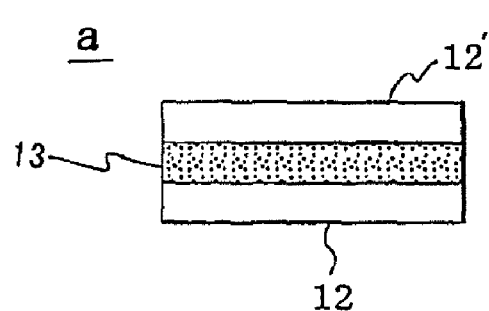
FIG. 10 is a cross-sectional view showing a related-art oral preparation.
Figure 10:
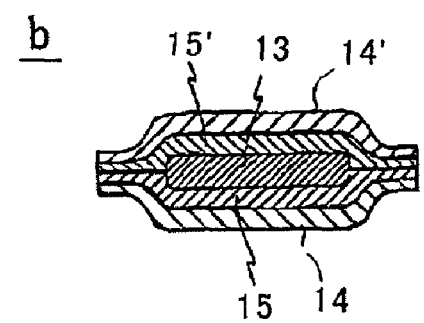

There are no particular limitations to the die-cut pattern. A die-cut pattern in which the sheet is cut only in the widthwise direction, a die-cut pattern sheet cut in the lengthwise and widthwise directions, and the like can be given. FIG. 9 shows examples of the die-cut pattern. FIG. 9(a) shows an example of die-cutting in the widthwise direction for producing sheets to be divided in pieces each containing three tablets, and FIG. 9(b) shows an example of die-cutting in the widthwise and lengthwise directions to produce a sheet to be divided in pieces each containing one tablet as shown in dotted lines.

According to the continuous process of the present invention, an oral preparation in which the medicine is completely masked so that the medicine can be administered without a problem of bitterness and odor can be simply, efficiently, and continuously produced without causing the medicine to deteriorate due to heat history, without a loss of the medicine, and without a limitation to the amount of the medicine to be added. Therefore, the process of the present invention is suitable for industrial production.

EXAMPLES

The present invention is further described below by way of examples. However, these examples should not be construed as limiting the present invention.

Example 1

(a) Formation of Water-Swellable Gel-Forming Layer 0.90 g of calcium chloride (Japanese Pharmacopoeia calcium chloride, manufactured by Tomita Pharmaceutical Co., Ltd.) was added to 900 g of purified water, and the mixture was stirred. 33.80 g of polyacrylic acid (Carbopole 974P, manufactured by CBC) was gradually added to the mixture with stirring, and the mixture was stirred for a further one hour. Next, 56.50 g of polyvinyl alcohol (Gohsenol EG40, manufactured by Nippon Synthetic Chemical Industry Co., Ltd.) was slowly added to the mixture, and the mixture was stirred at 70° C. for a further one hour. After the addition of 8.00 g of glycerol (Japanese Pharmacopoeia concentrated glycerol, manufactured by Asahi Denka Kogyo Co., Ltd., hereinafter the same) and 0.80 g of acesulfame potassium (Sunett A type, manufactured by Maruzen Pharmaceuticals Co., Ltd.), the mixture was stirred for 10 minutes to obtain a coating solution A.

The coating solution A was sufficiently defoamed, and spread over one side of a polyethylene terephthalate film (SP-PET3811 manufactured by LINTEC), of which the opposite side was treated with a release agent, using an applicator with a gap adjusted to make the amount of the coating after drying 10 g/m². The coating was dried at 80° C. for five minutes to obtain a water-swellable gel-forming layer.

(b) Formation of Adhesive Layer 91.00 g of polyvinylpyrrolidone (PVP K-90 manufactured by ISP Japan, Ltd.) was slowly added to 300 g of purified water, and the mixture was stirred for one hour. After the addition of 9.00 g of glycerol, the mixture was stirred for 10 minutes to prepare a coating solution B.

The coating solution B was sufficiently defoamed, and spread over the water-swellable gel-forming layer using an applicator with a gap adjusted to make the amount of the coating after drying 10 g/m². The resulting coating was dried at 80° C. for five minutes to obtain an adhesive layer.

A polyethylene terephthalate film (SP-PET3811 manufactured by LINTEC) was laminated on the adhesive layer as a protective film.

(c) Embossing

The surface of the protective film of the film obtained by (b) was embossed using an emboss roll shown in FIG. 6 to form recesses having a diameter of 15 mm and a depth of 0.5 mm.

(d) Filling with Medicine

After removing the protective film from the film obtained by (c), the recesses were filled with 10 mg of a famotidine (antiulcer drug) powder.

(e) Lamination

A film in which a water-swellable gel-forming layer and an adhesive layer were formed on a polyester terephthalate film was prepared in the same manner as in the above steps (a) and (b).

The film was thermally bonded to the above medicine-containing film obtained by (d) at a temperature of 100° C. and a pressure of 9.8×kgf/cm² for two seconds.

The film was die-cut to a diameter of 25 mm to obtain an oral preparation sample 1.

Comparative Example 1

(a) Formation of Water-Swellable Gel-Forming Layer

A water-swellable gel-forming layer was prepared in the same manner as in Example 1.

(b) Formation of Medicine-Containing Layer 68.25 g of polyvinylpyrrolidone (PVP K-90 manufactured by ISP Japan, Ltd.) was slowly added to 400 g of purified water, and the mixture was stirred for one hour. 25.00 g of Famotidine was slowly added to the mixture with stirring, and the resulting mixture was stirred for a further five minutes. After the addition of 6.75 g of glycerol, the mixture was stirred for 10 minutes to prepare a coating solution C.

The coating solution C was sufficiently defoamed, and spread over the water-swellable gel-forming layer obtained by (a) using an applicator with a gap adjusted to make the amount of the coating after drying 41 g/m². The resulting coating was dried at 85° C. for five minutes to obtain a medicine-containing layer.

(e) Lamination

Two sheets of the laminated films prepared by (b) were superimposed with the medicine-containing layers vis-a-vis facing, and thermally bonded at a temperature of 100° C. and pressure of 9.8×kgf/cm² for two seconds.

The resulting film was die-cut to a diameter of 25 mm to obtain an oral preparation sample 2.
(Bitterness Test)
A bitterness test of the oral preparations obtained in Example 1 and Comparative Example 1 was carried out as follows.

Subjects gargled to wash the mouth, put a sample into the mouth after two minutes, and brought out the sample 30 seconds thereafter. Bitterness felt by the subjects while the sample was in the mouth was evaluated according to the following standards. Evaluation 2 is a result between Evaluation 1 and Evaluation 3, and Evaluation 4 is a result between Evaluation 3 and Evaluation 5.
Evaluation 1: Bitterness was strong and unpleasant
Evaluation 3: Bitterness could be ignored
Evaluation 5: No bitterness
The evaluation results for the samples 1 and 2 are shown in Table 1.

TABLE 1

|  | Bitterness evaluation |
| --- | --- |
| Example 1 | 5 |
| Comparative Example 1 | 2 |

It can be seen from Table 1 that the oral preparation of Example 1 can be administered without imparting any bitterness at all. On the other hand, the oral preparation of Comparative Example 1 imparted significantly strong bitterness, indicating its low medication compliance.

The invention claimed is:
1. A process for producing an oral preparation containing a first water-swellable gel-forming layer and a second water-swellable gel-forming layer as outermost layers, a medicine being sealed in an inner space formed by bonding the periphery of the first water-swellable gel-forming layer and the periphery of the second water-swellable gel-forming layer directly or via an adhesive layer, the process comprising, sequentially, the steps of:
forming a first water-swellable gel-forming layer on a first supporting body;
forming a recess in a predetermined area of the first water-swellable gel-forming layer by pressing the predetermined area of the first water-swellable gel-forming layer;
filling the recess with a medicine to obtain a medicine-containing body; and
forming a second water-swellable gel-forming layer over the medicine-containing body directly or via an adhesive layer so that the first water-swellable gel-forming layer and the second water-swellable gel-forming layer are bonded around the recess;
wherein the step of forming a second water-swellable gel-forming layer comprises either:
obtaining a laminate by forming a second water-swellable gel-forming layer on a second supporting body and layering the laminate on the medicine-containing body by heat bonding, with the second water-swellable gel-forming layer side being on the side of the medicine-containing body on which the medicine is exposed, and removing the second supporting body; or
obtaining a laminate by forming a second water-swellable gel-forming layer and an adhesive layer on a second supporting body and layering the laminate on the medicine-containing body by heat bonding, with the adhesive layer side being on the side of the medicine-containing body on which the medicine is exposed, and removing the second supporting body.

2. The process according to claim 1, wherein the step of forming a recess in a predetermined area of the first water-swellable gel-forming layer includes a step of forming the recess by laminating a protective film on the first water-swellable gel-forming layer before forming the recess, and removing the protective film after forming the recess.

3. A process for producing an oral preparation containing a first water-swellable gel-forming layer and a second water-swellable gel-forming layer as outermost layers, a medicine being sealed in an inner space formed by bonding the periphery of the first water-swellable gel-forming layer and the periphery of the second water-swellable gel-forming layer directly or via an adhesive layer, the process comprising, sequentially, the steps of:
forming a first water-swellable gel-forming layer on a long first supporting body;
forming an adhesive layer on the first water-swellable gel-forming layer;
forming a number of recesses by pressing predetermined areas of the adhesive layer formed on the first water-swellable gel-forming layer with a working roll having a number of projections;
filling the recesses with a medicine to form a continuous band of a medicine-containing body; and
forming a second water-swellable gel-forming layer over the medicine-containing body directly or via an adhesive layer so that the first water-swellable gel-forming layer and the second water-swellable gel-forming layer are bonded around the recesses;
wherein the step of forming a second water-swellable gel-forming layer comprises either:
obtaining a laminate by forming a second water-swellable gel-forming layer on a long second supporting body and layering the laminate on the medicine-containing body by heat bonding, with the second water-swellable gel-forming layer side being on the side of the medicine-containing body on which the medicine is exposed, and removing the second supporting body, or
obtaining a laminate by forming a second water-swellable gel-forming layer and an adhesive layer on a long second supporting body, and layering the laminate on the medicine-containing body by heat bonding, with the adhesive layer side of the laminate being on the side of the medicine-containing body on which the medicine is exposed, and removing the second supporting body.

4. The process according to claim 3, wherein the step of forming a number of recesses includes a step of laminating a protective film on the adhesive layer before forming the recess, and removing the protective film after forming the recess.

5. A process for producing an oral preparation containing a first water-swellable gel-forming layer and a second water-swellable gel-forming layer as outermost layers, a medicine being sealed in an inner space formed by bonding the periphery of the first water-swellable gel-forming layer and the periphery of the second water-swellable gel-forming layer directly or via an adhesive layer, the process comprising, sequentially, the steps of:
- forming a first water-swellable gel-forming layer on a first supporting body;
- forming an adhesive layer on the first supporting body;
- forming a recess on the adhesive layer formed on the first water-swellable gel-forming layer by pressing a predetermined area of the adhesive layer;
- filling the recess with a medicine to obtain a medicine-containing body; and
- forming a second water-swellable gel-forming layer over the medicine-containing body directly or via an adhesive layer so that the first water-swellable gel-forming layer and the second water-swellable gel-forming layer are bonded around the recess;
- wherein the step of forming a second water-swellable gel-forming layer comprises either:
  - obtaining a laminate by forming a second water-swellable gel-forming layer on a second supporting body and layering the laminate on the medicine-containing body by heat bonding, with a second water-swellable gel-forming layer side being on a side of the medicine-containing body on which the medicine is exposed, and removing the second second supporting body, or
  - obtaining a laminate by forming a second water-swellable gel-forming layer and an adhesive layer on a second supporting body and layering the laminate on the medicine-containing body by heat bonding, with an adhesive layer side being on a side of the medicine-containing body on which the medicine is exposed, and removing the second supporting body.

6. The process according to claim 5, wherein the step of forming a recess includes a step of forming a laminate of a protective film on the adhesive layer formed on the first water-swellable gel-forming layer before forming the recess, and removing the protective film after forming the recess.

7. The process according to claim 1, 3 or 5, wherein the recess is formed by embossing.

8. The process according to claim 1, 3 or 5, wherein the medicine is a powder or a tablet.

9. The process according to claim 1, 3 or 5, wherein the first water-swellable gel-forming layer or the second water-swellable gel-forming layer includes at least one water-swellable gel-forming agent selected from the group consisting of a carboxyvinyl polymer, starch, starch derivatives, agar, alginic acid, arabino galactan, galactomannan, cellulose, cellulose derivatives, carrageen, dextran, tragacanth, gelatin, pectin, hyaluronic acid, gellan gum, collagen, casein, and xanthan gum.

10. The process according to claim 1, 3 or 5, wherein the first water-swellable gel-forming layer or the second water-swellable gel-forming layer includes a film-forming agent.

11. The process according to claim 1, 3 or 5, wherein the first water-swellable gel-forming layer or the second water-swellable gel-forming layer includes at least one film-forming agent selected from the group consisting of polyvinyl alcohol, polyvinylpyrrolidone, polyvinyl acetate, polyvinyl acetate phthalate, hydroxyalkyl celluloses, alkyl celluloses, carboxyalkyl celluloses, and (meth)acrylic esters.

12. The process according to claim 1, 3 or 5, wherein the first water-swellable gel-forming layer or the second water-swellable gel-forming layer includes a masking agent.

13. The process according to claim 1, 3 or 5, wherein the first water-swellable gel-forming layer or the second water-swellable gel-forming layer includes at least one masking agent selected from the group consisting of masking agents for providing acidity, sweeteners, fresheners, natural perfumes and synthetic perfumes.

14. The process according to claim 1, 3 or 5, wherein the adhesive layer includes at least one material selected from the group consisting of a carboxyvinyl polymer, polyacrylic acids, pharmacologically acceptable nontoxic salts of polyacrylic acids, an acrylate copolymer, pharmacologically acceptable nontoxic salts of an acrylate copolymer, hydrophilic cellulose derivatives, pullulan, povidone, karaya gum, pectin, xanthan gum, traganth, alginic acid, gum arabic, acid polysaccharides, acid polysaccharide derivatives, pharmacologically acceptable salts of acid polysaccharides, polyvinyl acetate, polyvinylpyrrolidone, and a copolymer of vinyl acetate and vinylpyrrolidone.

15. The process according to claim 1, 3 or 5, wherein the recess has a depth of 0.3 to 6 mm.

16. The process according to claim 1, 3 or 5, wherein the recess has a round shape and a diameter of 5 to 20 mm.

* * * * *